United States Patent [19]

Chang et al.

[11] 4,230,930
[45] Oct. 28, 1980

[54] LASER WELDING METHOD FOR ELECTRICAL WIRE CONNECTION TO A TERMINAL PIN OF AN EXHAUST GAS SENSOR

[75] Inventors: Uck I. Chang, Farmington Hills; Kenneth W. Casey, Westland, both of Mich.

[73] Assignee: Ford Motor Company, Dearborn, Mich.

[21] Appl. No.: 6,943

[22] Filed: Jan. 25, 1979

[51] Int. Cl.³ .............................................. B23K 27/00
[52] U.S. Cl. .............................. 219/121 LD; 338/329
[58] Field of Search ........... 219/121 L, 121 LM, 56.1, 219/56.22, 85 F, 85 BA, 121 LD, 121 LC, 121 PJ, 121 PK; 338/329, 322

[56] References Cited

U.S. PATENT DOCUMENTS

| | | | |
|---|---|---|---|
| 3,132,238 | 5/1964 | Wiley, Jr. et al. | 219/56.22 |
| 3,304,403 | 2/1967 | Harper | 219/121 L |
| 3,668,367 | 5/1972 | Keller et al. | 219/121 L |
| 3,944,777 | 3/1976 | Porat | 219/56.22 |
| 4,003,014 | 1/1977 | Branson et al. | 338/329 X |
| 4,136,258 | 1/1979 | Hansler | 219/121 LM |

OTHER PUBLICATIONS

S. R. Bolin et al., SME Publication, "Precision Pulsed Laser Welding", MR 75-751 (1975).
David C. Anderson, SME Publication," Laser Welding and Cutting Systems," MR 76-856 (1976).
Simon L. Engel, SME Publication, "Tooling Up for Laser Welding," MR 76-873 (1976).
James H. Mason, et al., SME Publication, "Spot and Continuous Welding with Solid State Lasers, "MR 74-955 (1974).

*Primary Examiner*—C. L. Albritton
*Attorney, Agent, or Firm*—Robert W. Brown; Clifford L. Sadler

[57] ABSTRACT

A method for welding an electrical lead wire to a terminal pin with the use of a laser beam. The method is particularly designed for use in welding an electrical lead wire of an exhaust gas sensor to a terminal pin having an opening through which the electrical lead wire extends to the exterior of the pin. The lead wire may be made of nichrome material and the terminal pin from leaded steel. The laser beam is positioned vertically above the extended portion of the lead wire and its focal point is above the end of the lead wire. No separate filler metal is required since the lead wire material is itself available as a filler material.

11 Claims, 8 Drawing Figures

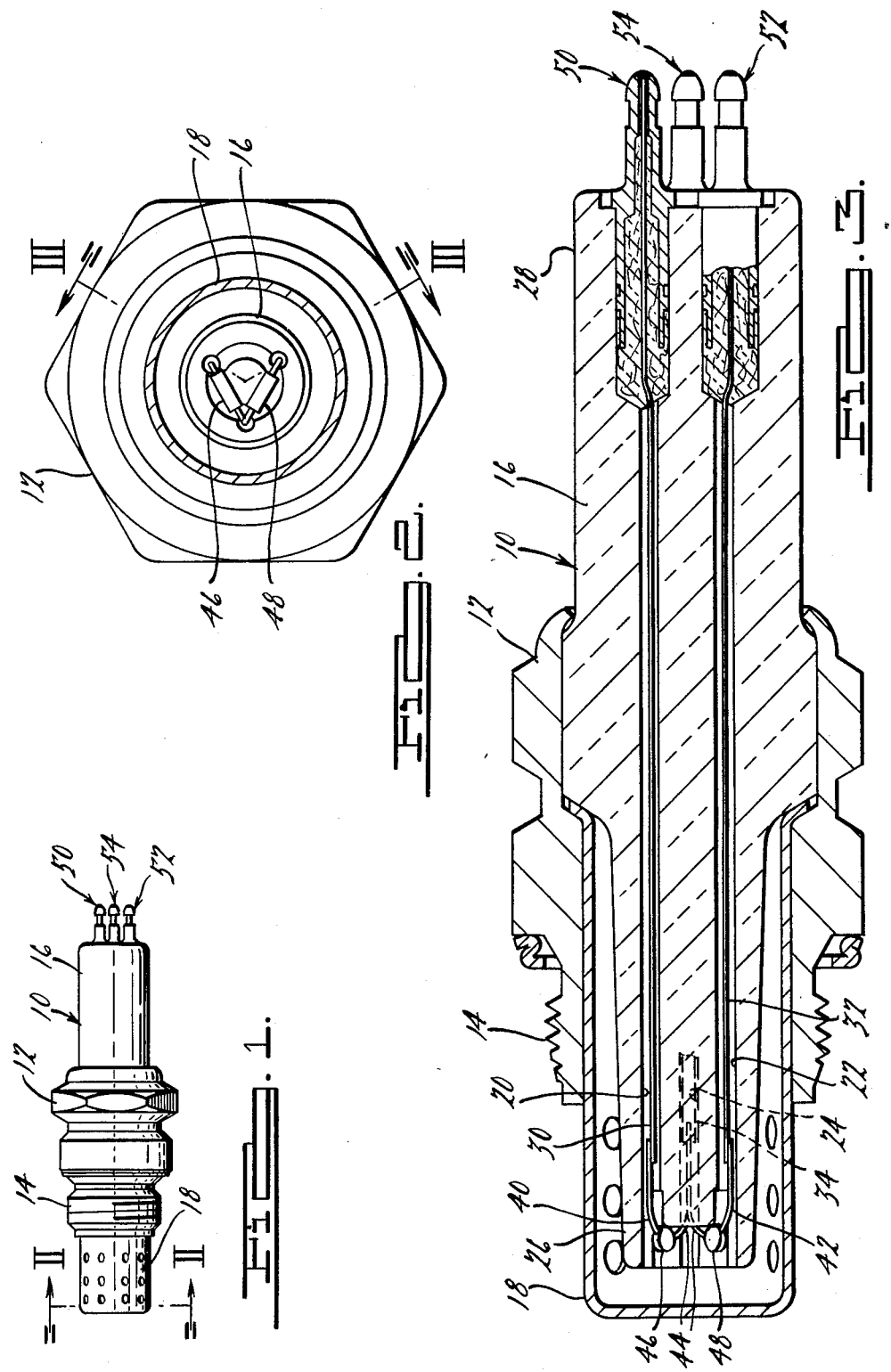

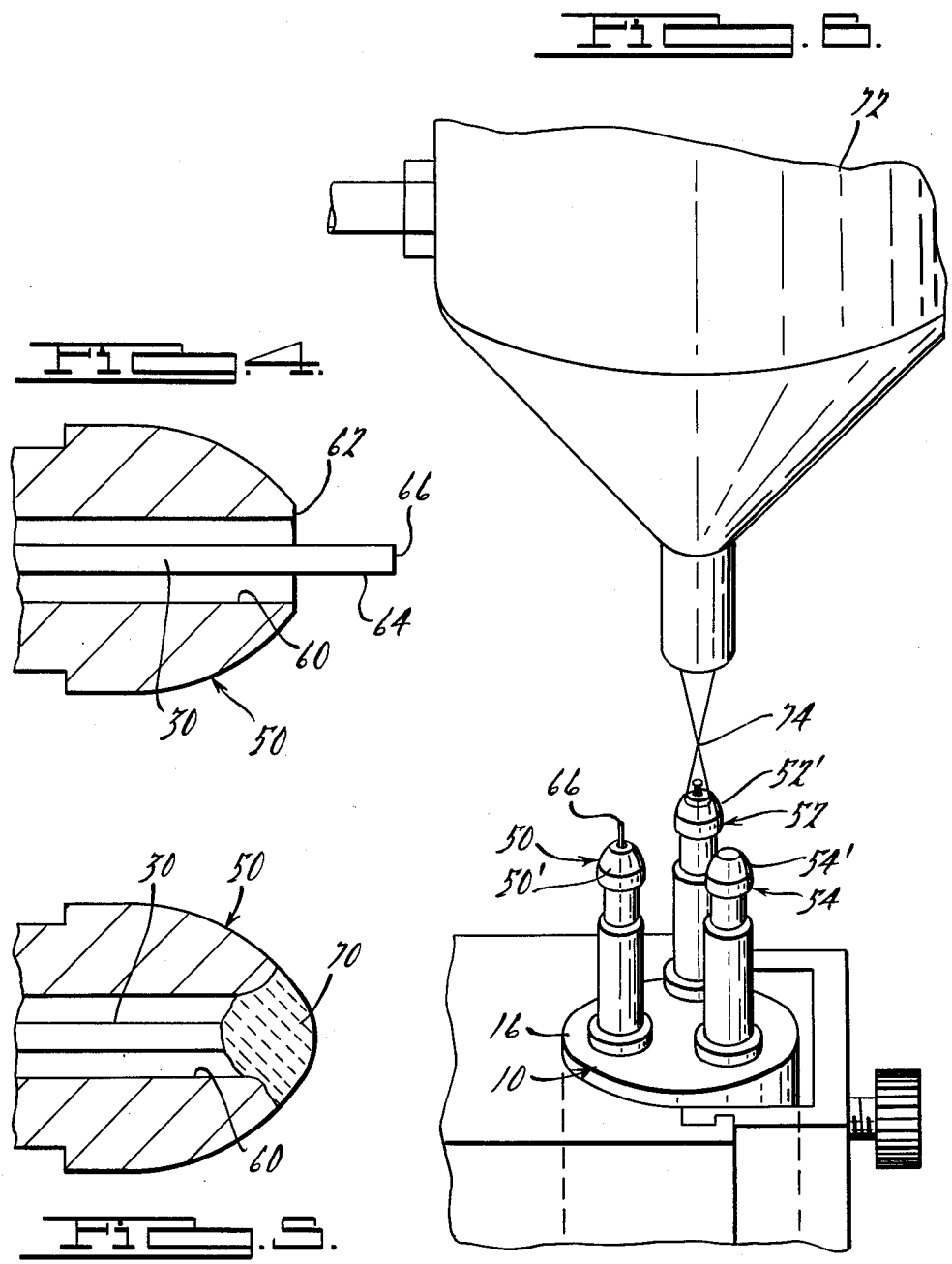

LASER WELDING METHOD FOR ELECTRICAL WIRE CONNECTION TO A TERMINAL PIN OF AN EXHAUST GAS SENSOR

CITATION OF PUBLICATIONS

The following technical papers, all of which are publications of the Society of Manufacturing Engineers, Dearborn, Michigan, are cited as of interest with respect to the subject matter hereof:

S. R. Bolin and E. T. Maloney, "Precision Pulsed Laser Welding," MR75-751 (1975).

David G. Anderson, "Laser Welding and Cutting Systems," MR76-856 (1976).

Simon L. Engel, "Tooling Up for Laser Welding," MR76-873 (1976).

James H. Mason and John H. Wasko, "Spot and Continuous Welding with Solid State Lasers," MR74-955 (1974).

BACKGROUND OF THE INVENTION

This invention relates to a method for welding an electrical lead wire to a terminal pin having a head with an internal opening, the electrical lead wire being received within the opening and having a portion extending to the exterior of the terminal-pin head. More particularly, the invention relates to a method for welding an electrical lead wire extending from the terminal pin of an exhaust gas sensor of the type having one or more ceramic, metal-oxide, oxygen-sensing elements supported by a ceramic insulator mounted in a steel body.

The steel body of the exhaust gas sensor is adapted to be positioned in an exhaust conduit through which flow exhaust gases from an internal combustion engine. The ceramic insulator supporting the oxygen-sensing element has one or more passages through each of which an electrical lead wire from the oxygen-sensing element passes for connection to a terminal pin mounted in the terminal-pin end of the exhaust gas sensor. The lead wire extends through an opening in the terminal-pin head and is welded to the terminal-pin head in accordance with the method of the invention. Prior to welding, the lead wire extends above the terminal-pin head.

SUMMARY OF THE INVENTION

In accordance with the welding method of the invention, a terminal pin for an exhaust gas oxygen sensor or other device is supported such that a portion of an electrical lead wire extending from the terminal-pin head is substantially vertical. The terminal pin, if used for electrical connection to an exhaust gas oxygen sensor, at the time of welding may be physically mounted in the sensor ceramic insulator. In any case, the electrical lead wire extending from the terminal pin is positioned so that an end of the electrical lead wire terminates a predetermined distance above the terminal-pin head. The terminal-pin head may have a spherical or semi-spherical shape with a flat surface at its tip, although other tip geometries are not precluded.

A laser beam source is positioned above the exterior portion of the electrical lead wire. The laser beam then is caused to be propagated in a direction substantially coinciding with the force of gravity. The laser beam thus is directed toward the ground and is positioned such that the laser beam has a focal point located above the end of the electrical lead wire, the laser beam impinging on the lead wire end at a location beyond and below its focal point.

The laser beam is applied to the electrical lead wire as specified in the preceding paragraph for a time period sufficient to enable the end of the electrical lead wire located on the exterior of the terminal pin to liquify. The liquified metal of the lead wire forms a ball. The ball of molten metal progressively moves downward toward the terminal-pin head and grows in size during such movement. Metal in the terminal-pin head is concurrently liquified by the laser beam. When the ball of molten metal of the lead wire reaches the molten metal of the terminal-pin head, the metals coalesce and fusion occurs. Upon removal of the laser beam, a solid weld is formed.

These and other features of the invention may be better understood by reference to the detailed description which follows and to the drawings.

BRIEF DESCRIPTION OF THE DRAWINGS

FIG. 1 is an elevational view of a titania exhaust gas oxygen sensor suitable for installation in the intake manifold of an internal combustion engine;

FIG. 2 is a sectional end view, taken along the line II—II in FIG. 1, of the sensor of FIG. 1 and is shown in enlarged scale;

FIG. 3 is a sectional view, taken along the line III-—III in FIG. 2, showing the internal structure of the sensor of FIGS. 1 and 2;

FIG. 4 is a further enlarged sectional view of one of the terminal pins in the exhaust gas sensor of FIGS. 1 to 3 and shows an electrical lead wire extending from the terminal pin as it appears prior to laser welding;

FIG. 5 is an enlarged sectional view similar to FIG. 4, but shows the exhaust gas sensor terminal pin after laser welding;

FIG. 6 is a perspective view showing a fixtured exhaust gas sensor with its three terminal pins in a vertical position and the focus head of a GTE-Sylvania, Inc., 1.5 kilowatt laser positioned above the sensor;

DETAILED DESCRIPTION

Figure 7:
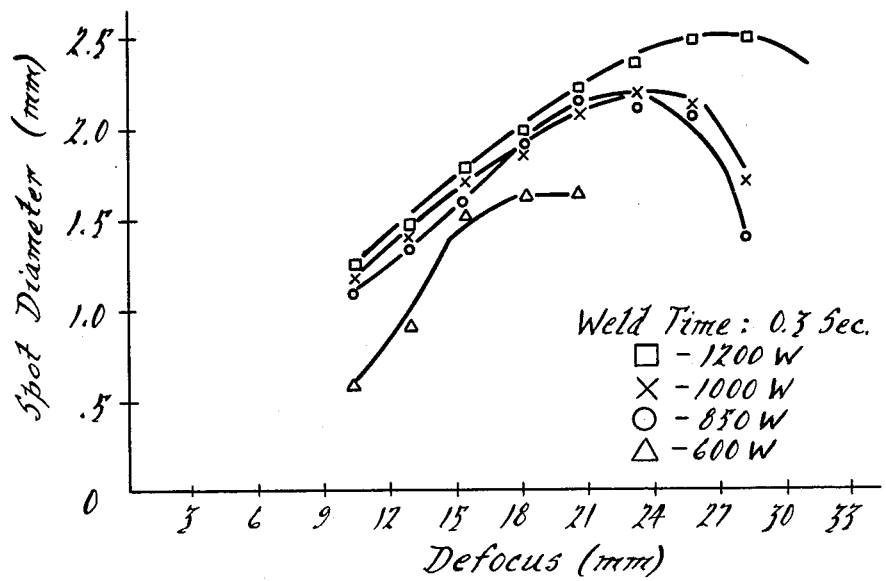
FIG. 7 is a graph illustrating laser weld spot diameter as a function of focal point distance (defocus) above a steel plate simulating the end of a terminal pin.

With particular reference now to the drawings, wherein like numerals refer to like parts in the several views, there is shown a complete titania exhaust gas sensor assembly generally designated by the numeral 10. The sensor includes a steel body 12, which may be substantially identical to a spark plug body, having a threaded portion 14 for engagement with a suitably threaded aperture provided within the exhaust system or exhaust conduit of an internal combustion engine (not shown). In most cases, the sensor 10 would be installed in an aperture in a location in the exhaust manifold or conduit near the flange that would connect to an exhaust pipe. A ceramic insulator 16 of circular cross-section extends through the body 12 and has a tapered portion 26 projecting outwardly from the body 12 into the volume defined by the boundaries of a perforated shield or protection tube 18. The projecting portion 26 of the insulator, among other things, acts as a support structure for an oxygen sensing element 46 and a thermistor 48. There are three longitudinal passages 20, 22 and 24 extending from the projecting end or portion 26 of the ceramic insulator to its opposite terminal portion or end 28. Wires 30, 32 and 34 are located in the respectively corresponding passages 20, 22 and 24 and are of a heat resistant character, preferably being made from an alloy such as 80% nickel/20% chrome wire. These electrically conductive wires are welded to precious-metal wire leads 40, 42 and 44, which are embedded in the disc-shaped ceramic, metal oxide, oxygen-sensing and thermistor elements 46 and 48.

Element 46 is a ceramic titania $O_2$ sensor responsive to the partial pressure of oxygen in the gaseous medium to which this element is exposed. The element 48 is a thermistor made from titania ceramic material of greater density than the density of the porous titania oxygen sensor 46. The thermistor 48 is intended to provide temperature compensation in accordance with the circuitry best described in commonly-assigned, concurrently-filed U.S. Patent application Ser. No. 5,422 entitled "Exhaust Gas Sensor Electrical Circuit Improvement."

The sensor of FIGS. 1 through 4 is intended to be used in conjunction with electronic circuitry for closed-loop feedback control of the amount of fuel supplied to an internal combustion engine. The sensor indicates whether the exhaust gases contain a substantial amount of HC and CO or whether instead there is a substantial amount of oxygen, thereby, indicating whether or not the air/fuel ratio of the mixture supplied to the engine was rich to lean with respect to the stoichiometric value of about 14.7 parts of air to each part of fuel by weight. This air/fuel ratio typically is expressed as a normalized air/fuel ratio lambda, wherein the actual ratio is divided by the stoichiometric value and the stoichiometric ratio therefore is represented as 1.0 in accordance with well-known practice.

The exhaust gas sensor 10 has terminal pins 50, 52 and 54 designed for connection to external circuitry as specified above to enable it to be used in a feedback fuel control system.

The ceramic metal oxide elements 46 and 48 are intended to operate over a temperature range extending from about 350° C. and 850° C. These elevated temperatures are produced primarily as a result of the location of the exhaust gas oxygen sensor 10 in the exhaust stream of an internal combustion engine. The sensor, therefore, is subjected repeatedly to wide variations in temperature. When installed in a motor vehicle the sensor 10 may be subjected to environmental temperatures as low as −40° C. When the vehicle is placed in operation, this temperature may rise to 500° or 600° C. in a very short time. Cyclical heating and cooling of the sensor 10 may occur several times each day in typical motor vehicle usage. This may be very hostile with respect to the bond formed between the terminal pins 50, 52 and 54 and the ceramic insulator 16 in which they are received.

With particular reference now to FIG. 4, there is shown an enlarged sectional view of the head portion of the terminal pin 50 as the terminal pin appears prior to welding of its nickel-chrome electrical lead wire 30 to the terminal pin. The terminal pin for welding preferably is made from a leaded steel material (AISI C 12L 14) having a copper flash plating followed by a nickel plating of low luster (semi-bright) finish. The terminal pin also may be made from low carbon steel (AISI 1018) and still be welded satisfactorily with the laser beam technique described more fully hereinafter.

The terminal pin 50 has a flat area 62 at the end of the spherically-shaped surface defining the terminal-pin head. The flat area 62 is adjacent the sharp entry edge of the internal opening 60 in the terminal-pin head through which the lead wire 30 passes. The portion 64 of the electrical lead wire 30 extends above the flat area 62 at the end of the terminal pin. The electrical lead wire 30 has an end or termination point 66 that is of importance with respect to the laser welding method of the invention. With the leaded-steel terminal-pin material and the nickel-chrome wire 30, of cross-sectional area substantially smaller than the cross-sectional area of the opening 60 through which the lead wire passes, it has been found that the distance between the end 66 of the electrical lead wire and the flat-surface 62 end of the terminal pin 50 should be between about 1.3 and 2.5 millimeters. This applies to a laser beam weld to be formed between an electrical lead wire having a diameter of about 0.43 millimeters and a terminal pin having an internal diameter for the opening 60 of about 0.69 millimeters.

With particular reference to FIG. 5, there is shown the terminal pin 50 as it appears after the weld between the electrical lead wire 30 and the terminal pin has been achieved. The weld area is designated by the numeral 70. It may be seen that the weld forms electrical connection between the lead wire and the terminal pin, as well as a gas-tight seal. In an exhaust gas sensor application, the gas-tight seal prevents leakage of exhaust gases through the terminal-pin area. In the sensor application, the terminal pin is retained within the ceramic insulator 16 with a Sauereisen No. 31 cement that also provides a sealing affect. Care must be taken during the laser beam welding to prevent contamination of the weld zone by the cement material.

FIG. 6 illustrates the manner in which laser welds are formed between the terminal pins 50, 52 and 54 and their respectively associated electrical lead wires. In FIG. 6, the end of the exhaust gas sensor 10 having the ceramic insulator 16 is supported such that the terminal-pin heads 50', 52' and 54' are positioned beneath a laser-beam focusing-head 72. The laser beam may be obtained from a commercially available GTE-Sylvania, Inc., Model No. 971 $CO_2$ laser welding device of 1.5 kilowatt capacity. The focusing head 72 is positioned and adjusted such that it has a focal point 74 in the laser beam it produces that is located a predetermined distance above the end 66 (FIG. 4) of the electrical lead wire on which the beam 76 from the focus head impinges. The laser beam is propagated in the direction of the force of gravity, that is, in a downward direction with respect to the vertically extending electrical lead wire being welded to a terminal pin. With the focal point of the laser beam above the end 66 of the lead wire, the laser beam spreads somewhat in the downward direction such that some of it preferably impinges on the head of the terminal pin being welded as well as on the end 66 of the electrical lead wire.

Upon application of the laser beam to the lead wire, the end 66 of the electrical lead wire liquifies forming a small ball that gradually progresses in a downward direction due to the force of gravity and surface tension acting thereon during the weld process. The ball of liquid metal gradually increases in diameter and reaches the flat area 62 at the head of the terminal pin; by the time the molten ball of electrical lead wire material reaches the flat area 62, there will have taken place a concurrent liquification of the terminal-pin metal adjacent the opening 60 in the terminal-pin head. Coalescence or fusion of the electrical lead wire metal with that of the terminal pin takes place. Upon termination of the laser beam impingement on the lead wire and terminal pin, the coalesced metals solidify to form a weld, as was shown in the sectional view of FIG. 5. FIG. 6 depicts the terminal pin 54 with a completed weld, the terminal pin 52 with a laser-beam weld in progress, and the terminal pin 50 with its lead wire extending above the terminal pin and untouched by the laser beam.

It may be noted that the opening 60 has a straight edge up to the flat portion 62 of the end of the terminal pin. It has been found desirable to have this straight, unchamfered edge at the end of the terminal pin as compared to a chamfered edge because the power requirement for the laser weld is approximately 200 watts less relative to that required with a chamfered edge. Also the straight edge of the opening 60 at the end 62 provides a useful reference line for determination of the terminal-pin melting.

It has been found that the length of the extending portion 64 of the electrical lead wires should be greater than two-thirds of the cube of the diameter of the opening 60 divided by the square of the diameter of the electrical lead wire. Also, the length of the extending portion 64 should be less than two-thirds of the cube of the diameter of the flat end 62 divided by the square of the electrical lead-wire diameter.

With particular reference now to FIG. 7, there is shown a graph of molten-metal spot diameter versus defocus length. The defocus length in the graph of FIG. 7 is the distance between the focal point of the laser beam and the location at which it impinges on the surface of, in this case, a 2.5 mm thick hot-rolled steel plate (AISI 1018). The laser-beam utilized in obtaining the test results illustrated in FIG. 7 was generated by a GTE, Sylvania Model 971 laser having a 5 inch focal length lens. The 4 curves in FIG. 7 illustrate the spot diameters which were molten at various laser beam power levels with a weld time somewhat in excess of 0.3 seconds. The 0.3 seconds was the indicated weld time established by a weld-time control device, but was found to be slightly less than the actual weld time. The end points of the curves in FIG. 7 indicate that the average power density required to melt the test plate material with a 0.3 seconds weld time is about $6.5 \times 10^5$ watts per $cm^2$.

In the use of the laser beam to weld an electrical lead wire to a terminal pin of an exhaust gas sensor, the focal point of the lens associated with the laser beam is positioned above the end 66 of the electrical lead wire and the beam impinges on such end at a point beyond or below the focal point of the laser beam. The laser beam concurrently impinges on the flat area 62 of the terminal pin. An additional portion of the terminal pin also may be exposed to the laser beam. The defocus distance and the laser beam power output may be varied to produce a weld of suitable quality.

Figure 8:
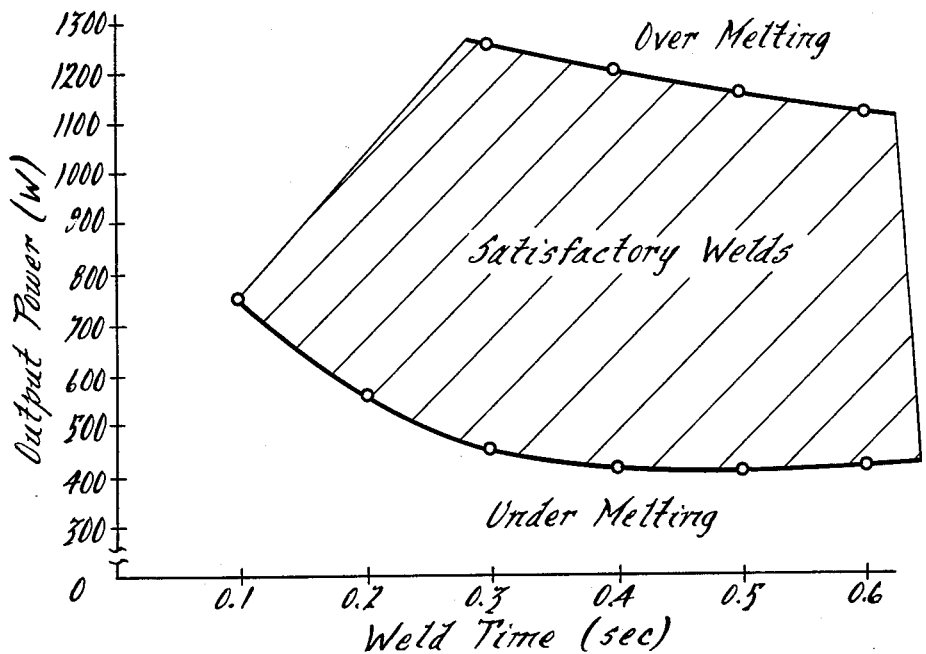
FIG. 8 is a weld lobe illustrating the combinations of laser output power and weld time that can be used to produce satisfactory exhaust sensor terminal-pin welds.

FIG. 8 illustrates a weld lobe (a graph of laser beam power versus weld time) illustrating the wide variation in laser beam power and weld time that may be used to produce satisfactory welds of an electrical lead wire to the head of a terminal pin of an exhaust gas sensor of the type illustrated in the drawings. The shaded area labelled "satisfactory welds" includes the preferred weld schedule, a weld time of 0.3 seconds with a laser beam output power of about 850 watts. This combination of laser beam output power and weld time produces welds having the most satisfactory melting and coalescence characteristics. In the lower curve, the weld quality is limited by undermelting, whereas above the limits established by the upper curve, overmelting of the metal in the terminal pin and electrical lead wire may occur.

It has been found desirable during welding to use a nitrogen shielding gas at a flow rate of 20 scfh and with a gas discharge nozzle located a distance of about 3.8 millimeters from the terminal-pin head. A wire of the diameter previously described and a terminal pin as described and illustrated desirably may be welded with an electrical lead wire extension distance 64 (the distance between the point 66 and the flat area 62) of about 2.3 millimeters. The defocusing distance may be 15.2 millimeters where a lens having a focal length of 127 millimeters is used. This weld schedule assumes that the terminal pin is aligned with the laser beam axis and that the weld area is free of contaminants. Also, the weld schedule applies to a laser beam produced by the aforementioned 1.5 kilowatt GTE Sylvania Model No. 971 $CO_2$ laser.

It should be particularly noted that no filler metal is required in the laser beam welding of the electrical lead wire to the terminal pin. As the electrical lead wire melts, the concurrent melting of the terminal-pin head and coalescence of the liquified metals results in filling of the opening 60 in the terminal-pin head.

Based upon the foregoing description of the invention,

What is claimed is:

1. A method for welding an electrical lead wire to a terminal pin, the terminal pin having a head with an internal opening, the electrical lead wire being received within the opening and having a portion extending to the exterior of the terminal-pin head, the method comprising the steps of:
    (a) supporting the terminal pin with the head thereof being located such that the portion of the electrical lead wire extending therefrom is substantially vertical and the exterior portion of the lead wire has its end terminating a predetermined distance above the terminal-pin head;
    (b) positioning a laser beam source above the exterior portion of the lead wire;
    (c) causing the laser beam from the source to be propagated in a direction substantially coinciding with the force of gravity, the laser beam having a focal point located above the electrical lead wire end and the laser beam impinging on the end of the electrical lead wire and on the head of the terminal pin; and
    (d) applying the laser beam to the electrical lead wire and terminal-pin head, as specified in step (c) above, for a time period sufficient to enable the end of the electrical lead wire to liquify, to progressively move in the liquified state toward the terminal-pin head, and thereafter to coalesce with metal in the terminal-pin head concurrently liquified by the laser beam.

2. A method for welding according to claim 1, wherein the coalescence is achieved in the absence of filler metal.

3. A welding method according to claim 1, wherein the coalescence of the electrical lead wire and the liquified terminal-pin head material forms an electrical connection between the terminal pin and the lead wire, seals the opening in the terminal pin from which the electrical lead wire extended, and forms a gas-tight seal at the end of the terminal-pin head.

4. A welding method according to claim 2, wherein the compositions of the terminal pin and the electrical lead wire are substantially different.

5. A welding method according to claim 4, wherein the terminal pin is formed from a steel composition and the electrical lead wire from a nickel-chrome composition.

6. A welding method according to claims 1 or 2, wherein the opening in the terminal-pin head has a cross-section substantially larger in area than the cross-sectional area of the electrical lead wire.

7. A welding method according to claims 1 or 2, which further includes the step of controlling the distance from the focal point of the laser beam to the end of the electrical lead wire prior to application of the laser beam to such end of the electrical lead wire.

8. A welding method according to claim 7, wherein the power density of the laser beam impinging on the end of the electrical lead wire is varied during the application of the laser beam thereto.

9. A welding method according to claim 7, wherein the terminal-pin material is made from a leaded steel composition and the electrical lead wire is made from a nickel-chrome composition.

10. A welding method according to claim 9, wherein the terminal pin material is leaded steel having a nickel plating thereon.

11. A welding method according to claim 10, wherein the nickel plating on the terminal pin is dull in appearance and has been applied over a flash plate of copper.

* * * * *